(12) United States Patent
Richards et al.

(10) Patent No.: US 10,444,157 B2
(45) Date of Patent: Oct. 15, 2019

(54) METHOD OF ASSESSING HAIR COLOUR CHANGES

(71) Applicant: Conopco, Inc., Englewood Cliffs, NJ (US)

(72) Inventors: Claire Louise Richards, Wrexham (GB); Neil Scott Shaw, Warrington (GB)

(73) Assignee: CONOPCO, INC., Englewood Cliffs, NJ (US)

(*) Notice: Subject to any disclaimer, the term of this patent is extended or adjusted under 35 U.S.C. 154(b) by 238 days.

(21) Appl. No.: 14/912,938

(22) PCT Filed: Sep. 1, 2014

(86) PCT No.: PCT/EP2014/068537
§ 371 (c)(1),
(2) Date: Feb. 19, 2016

(87) PCT Pub. No.: WO2015/032724
PCT Pub. Date: Mar. 12, 2015

(65) Prior Publication Data
US 2016/0202188 A1    Jul. 14, 2016

(30) Foreign Application Priority Data
Sep. 3, 2013 (EP) .................. 13182850

(51) Int. Cl.
C09B 67/44 (2006.01)
G01N 21/75 (2006.01)

(52) U.S. Cl.
CPC ......... *G01N 21/75* (2013.01); *C09B 67/0083* (2013.01)

(58) Field of Classification Search
CPC ...... G01N 21/75; C09B 67/0083; A61Q 5/12; A61Q 5/06; A61K 8/416; A61K 8/042; A61K 8/31; A61K 8/342; A61K 8/42; A61K 2800/49; A61K 2800/805
See application file for complete search history.

(56) References Cited

U.S. PATENT DOCUMENTS

| | | | | |
|---|---|---|---|---|
| 5,605,704 A | * | 2/1997 | Finel | A61K 8/14 424/450 |
| 2001/0007160 A1 | * | 7/2001 | Yamaguchi | A61K 8/34 8/405 |
| 2006/0075580 A1 | * | 4/2006 | Chan | A61K 8/416 8/405 |
| 2008/0241854 A1 | * | 10/2008 | Shmuylovich | G01N 33/52 435/7.1 |
| 2009/0104136 A1 | * | 4/2009 | Anderson | A61K 8/8152 424/70.9 |
| 2010/0028279 A1 | | 2/2010 | Carballada et al. | |
| 2011/0126363 A1 | | 6/2011 | Debain et al. | |
| 2011/0229430 A1 | * | 9/2011 | Hawkins | A61K 8/735 424/70.12 |
| 2012/0210520 A1 | | 8/2012 | Lim et al. | |

FOREIGN PATENT DOCUMENTS

| | | |
|---|---|---|
| CN | 101909587 | 12/2010 |
| EP | 1118319 A1 | 7/2001 |
| JP | 2011042584 | 3/2011 |
| JP | 2000169343 | 7/2018 |
| WO | WO0106994 | 2/2001 |
| WO | WO2009040354 A1 | 4/2009 |
| WO | WO2009068830 A2 | 6/2009 |
| WO | WO2009085838 A1 | 7/2009 |
| WO | WO2015032724 | 3/2015 |

OTHER PUBLICATIONS

Search Report & Written Opinin in EP13182850 dated Jan. 31, 2014. In J4359-NPLRef1, pp. 1 to 5.
Search Report & Written Opinion in PCTEP2014068537 dated May 12, 2014. In J4359-NPLRef2, pp. 1 to 10.
International Colour Charts for Hairdressing, Hair and Makeup Artist Handbook, Apr. 20, 2013, PP1-5Retrieved from the internet: http://hair-and-makeup-artist.com/international-colour-charts-hairdressing/.

* cited by examiner

*Primary Examiner* — Lore R Jarrett
(74) *Attorney, Agent, or Firm* — Foley & Lardner LLP

(57) ABSTRACT

The invention provides a method of assessing the potential color protecting effect in vivo of a test formulation such as rinse-off hair treatment formulation, the method comprising the steps of: providing a sample of the test formulation to be assessed; providing a model substrate in the form of a hair switch which has been artificially colored; applying the test formulation to the hair switch; subsequently rinsing the test formulation from the hair switch; collecting the rinse liquor and analysing it for the presence of eluted color; characterized in that the artificial color used to color the hair switch is a permanent hair colorant with a shade level 1 or 2 according to the International Color Chart (I.C.C.). The method provides improved sensitivity and differentiation, and enables the tester to compare different technologies in terms of effectiveness.

17 Claims, No Drawings

METHOD OF ASSESSING HAIR COLOUR CHANGES

FIELD OF INVENTION

This invention relates to a method of assessing hair colour changes, more particularly those hair colour changes which occur in oxidatively coloured hair due to shampoo or rinse-off conditioner application cycles.

BACKGROUND OF THE INVENTION AND PRIOR ART

The colouring of hair has become increasingly popular in recent years, and many different colouring systems have been developed for use in this context. There are generally three types of hair colouring system in widespread use: permanent, semi-permanent, or temporary.

Technology for permanent hair colorants has advanced significantly over the past decade. Consumers can achieve vibrant and multi-dimensional colour from these products and consequently have high expectations. It is particularly important that the colour maintains its vibrancy, intensity and original hue during normal wear. Colour fading can be initiated by environmental circumstances, such as by UV exposure. However the washing process is the most significant factor in the removal of hair colour. Some colouring components are more easily washed out during shampooing or rinse-off conditioner application, and this "washing-out" causes both fading and change of tone. In particular this is observed with red shades. Other sensory characteristics such as shine, body, lustrous feel and manageability are also linked to colour retention.

For this reason, specialized shampoos and conditioners have been designed specifically for hair treated with permanent colorants. For example, certain families of silicones such as amodimethicone and derivatives have been described as a colour-lock aid in rinse-off hair care products. WO2009/085838 describes a hair colour protection technology based upon the application of hydrophobically modified cationic polymers such as Polyquaternium-55. This is said to be most effective when formulated in a 3-step anti-fading system comprising shampoo, conditioner and leave-in treatment or styler.

A problem associated with hair colour protection technologies is that is difficult to evaluate their effectiveness. Current methodologies for assessing the hair colour changes which are attributable to "washing-out" tend to give hugely variable results. Often they are not sufficiently sensitive or differentiating, which makes it impossible for the tester to compare different technologies in terms of effectiveness.

The present invention provides a solution to this problem.

SUMMARY OF THE INVENTION

The present invention provides a method of assessing the potential colour protecting effect in vivo of a test formulation such as a rinse-off hair treatment formulation, the method comprising the steps of:

providing a sample of the test formulation to be assessed;
providing a model substrate in the form of a hair switch which has been artificially coloured;
applying the test formulation to the hair switch;
subsequently rinsing the test formulation from the hair switch;
collecting the rinse liquor and analysing it for the presence of eluted colour;

characterised in that the artificial colour used to colour the hair switch is a permanent hair colorant with a shade level 1 or 2 according to the International Colour Chart (I.C.C.).

DETAILED DESCRIPTION OF THE INVENTION

As described above, in the assessment method of the invention the artificial colour used to colour the hair switch is a permanent hair colorant with a shade level 1 or 2 according to the International Colour Chart (I.C.C.).

The International Colour Chart (I.C.C.) is a numerical system used worldwide to classify hair colour. It means that each hair colour has a definition that is recognised around the globe, and can be used by manufacturers on hair colour charts and tubes or boxes of hair dyes. Essentially, the I.C.C system uses numbers to convey what the shade level of the colour is, and what tones (if any) are in the colour.

The shade level of a hair colour (also termed its depth) refers to its lightness or darkness. Words such as light, medium, dark, palest, darkest and very light convey a hair colour's shade level.

The I.C.C. system assigns a number for measuring dark to light without regard to tonal value. Shade level is given a whole number from 1 to 10, where 1 is the darkest hair colour (black) and 10 is the lightest (lightest blonde). Some manufacturers also use 11 and 12 on their colouring products to account for the blondest of the blonde.

The tone of a colour is how warm or cool the colour is, and includes colours like red, gold, ash, and pearl.

Hair colouring products can have just the base colour without any tones, or they can have up to three or four tones. One or two tones are most commonly seen.

Whilst the shade level of the colour is a universal system shared by all brands, the tonal notations often vary a lot between different manufacturers.

Typically, numbers that come after the shade level (depth) number symbolise the tone of the colour. The tonal numbers are usually separated from the shade level number by a dividing symbol like a decimal point, a slash or a hyphen.

The first tonal number is the primary or dominant tone, meaning that it is the strongest tone, with more influence over the final colour, than any other tones (if they are present). Tones are generally numbered from 0.0 to 0.9, although some manufacturers use letters to represent the different tones e.g. R for red, or M for mahogany.

The term "permanent hair colorant" in the context of the present invention generally refers to oxidative hair colouring agents in which oxidative dye precursors diffuse into the hair through the cuticle and into the cortex, where they can then undergo oxidative coupling reactions in the presence of suitable oxidizing agents to form the end dye molecules which produce colour inside the hair.

Permanent hair colorants are typically formulated in two parts: one part containing the hair colorant, which incorporates oxidative dye precursors; and the other part containing the colour developer, which incorporates the oxidizing agent.

In order to colour the hair, the hair colorant and colour developer are mixed together, usually shortly before use. On the hair, the mixture forms a stable formulation with enough consistency and body to remain on the hair without dripping or running during the colouring period. The oxidative dye precursors diffuse into the hair together with the oxidizing agent from the colour developer.

The dyes form within the hair fibre. Being large molecules, they remain in the hair and do not readily wash out with ordinary shampoos. At the end of the colouring period, (generally about 5 to 45 minutes and preferably about 10 to 30 minutes), the formulation is washed from the hair with a plain water rinse. If necessary, the hair is washed with a shampoo and rinsed, for example with water or a weakly acidic solution, such as a citric acid or tartaric acid solution, and dried. Optionally, a separate conditioning product may also be applied.

The hair colorant part suitably comprises one or more oxidative dye precursors that are operable, when combined with an aqueous oxidizing agent, to impart colour to the hair. Generally such oxidative dye precursors include primary intermediates and optionally couplers for the formation of oxidative dyes. Primary intermediates yield colour on oxidation. Couplers do not form dyes on oxidation but do produce colour changes when used with primary intermediates.

Primary intermediates mainly belong to three classes of aromatic compounds: diamines, aminophenols and phenols.

Examples include ortho or para-substituted aminophenols or phenylenediamines and cosmetically acceptable salts thereof.

The term "cosmetically acceptable" in the context of the present invention means that ingredients which the term describes are suitable for use in contact with the skin or hair of humans and lower animals without undue toxicity, incompatibility, instability, irritation, allergic response, and the like.

Suitable primary intermediates for use in the hair colorant part include:

p-phenylenediamines such as: benzene-1,4-diamine (commonly known as p-phenylenediamine or PPD), 2-methyl-benzene-1,4-diamine (commonly known as p-toluenediamine or PTD); 2-[(4-aminophenyl)-(2-hydroxyethyl)-amino]-ethanol, (commonly known as N,N-bis(2-hydroxyethyl)-p-phenylenediamine); 2-chloro-p-phenylenediamine; N-phenyl-p-phenylenediamine; N-2-methoxyethyl-p-phenylenediamine; N,N-bis-(2-hydroxyethyl)-p-phenylenediamine; 2-hydroxymethyl-p-phenylenediamine; 2-hydroxyethyl-p-phenylenediamine; 4,4'-diaminodiphenylamine; 2,6-dimethyl-p-phenylenediamine; 2-isopropyl-p-phenylenediamine; N-(2-hydroxypropyl)-p-phenylenediamine; 2-propyl-p-phenylenediamine; 1,3-bis-(N-hydroxyethyl)-N-(4-aminophenyl)amino)-2-propanol; 2-methyl-4-dimethylaminoaniline; and cosmetically acceptable salts thereof and combinations thereof. Preferred p-phenylenediamines include: p-toluenediamine; p-phenylenediamine; N-2-methoxyethyl-p-phenylenediamine; N,N-bis-(2-hydroxyethyl)-p-phenylenediamine; 2-hydroxyethyl-p-phenylenediamine; and cosmetically acceptable salts thereof and combinations thereof.

p-aminophenols such as: 4-aminophenol (commonly known as p-aminophenol); p-methylaminophenol; 3-methyl-p-aminophenol; 2-hydroxymethyl-p-aminophenol; 2-methyl-p-aminophenol; 2-(2'-hydroxyethylaminomethyl)-p-aminophenol; 2-methoxymethyl-p-aminophenol; 5-aminosalicylic acid; and cosmetically acceptable salts thereof and combinations thereof. Preferred p-aminophenol derivatives include: p-aminophenol; p-methylaminophenol; 3-methyl-p-aminophenol; 2-methyl-p-aminophenol; 2-(2'-hydroxyethylaminomethyl)-p-aminophenol; 2-methoxymethyl-p-aminophenol; 5-aminosalicylic acid; and cosmetically acceptable salts thereof and combinations thereof.

o-phenylenediamines such as: 3,4-diaminobenzoic acid and cosmetically acceptable salts thereof.

o-aminophenols such as: 2-aminophenol (commonly known as o-aminophenol); 2,4-diaminophenol; 2-amino-5-methyl-phenol; 2-amino-6-methyl-phenol; N-(4-amino-3-hydroxy-phenyl)-acetamide; 2-amino-4-methyl-phenol; and cosmetically acceptable salts thereof and combinations thereof.

heterocyclics such as: pyrimidine-2,4,5,6-tetramine; 1-methyl-1H-pyrazole-4,5-diamine; 2-(4,5-diamino-1H-pyrazol-1-yl)ethanol; 1-(4-methylbenzyl)-1H-pyrazole-4,5-diamine; 1-(benzyl)-1H-pyrazole-4,5-diamine; 2-N,2-N-dimethyl-pyridine-2,5-diamine; 1-(4-aminophenyl)-2-pyrrolidinemethanol; N-(4-aminophenyl)-4-hydroxy-2-pyrrolidinemethanol; 4-hydroxy-2,5,6-triaminopyrimidine; 1-(2'hydroxyethyl)-amino-3,4-methylene dioxybenzene; 1-hydroxyethyl-4,5-diaminopyrazole; and cosmetically acceptable salts thereof and combinations thereof.

Particularly preferred primary intermediates include: p-phenylenediamine; p-toluenediamine; p-aminophenol; 3-methyl-p-aminophenol; N,N-bis(2-hydroxyethyl)-p-phenylenediamine; 2-hydroxyethyl-p-phenylenediamine; 1-hydroxyethyl-4,5-diaminopyrazole; and cosmetically acceptable salts thereof and combinations thereof.

Mixtures of any of the above-described materials may also be used.

Primary intermediates are generally used in approximately equimolar quantities with respect to couplers, for example at a molar ratio of primary intermediate to coupler from 0.95 to 1.05, although the relative quantities may vary depending upon the formulation and the desired color, intensity or effect.

Couplers are generally meta-derivatives such as phenol, resorcinol and naphthol derivatives, m-aminophenols and m-phenylenediamines; which may be unsubstituted, or substituted on the amino group or benzene ring with alkyl, hydroxyalkyl or alkylamino groups.

Suitable couplers for use in the hair colorant part include:

phenol, resorcinol and naphthol derivatives such as: naphthalene-1,7-diol; benzene-1,3-diol (commonly known as resorcinol); 4-chlorobenzene-1,3-diol (commonly known as 4-chlororesorcinol); naphthalen-1-ol (commonly known as 1-naphthol); 2-methyl-naphthalen-1-ol; naphthalene-1,5-diol; naphthalene-2,7-diol, benzene-1,4-diol; 2-methyl-benzene-1,3-diol (commonly known as 2-methylresorcinol); 7-amino-4-hydroxy-naphthalene-2-sulfonic acid; 2-isopropyl-5-methylphenol; 1,2,3,4-tetrahydro-naphthalene-1,5-diol; 2-chloro-benzene-1,3-diol; 4-hydroxy-naphthalene-1-sulfonic acid; benzene-1,2,3-triol; naphthalene-2,3-diol; 5-dichloro-2-methylbenzene-1,3-diol; 4,6-dichlorobenzene-1,3-diol; 2,3-dihydroxy-[1,4]-naphthoquinone; 1-acetoxy-2-methylnaphthalene; and cosmetically acceptable salts thereof and combinations thereof.

m-phenylenediamines such as: m-phenylenediamine; 2,4-diaminophenoxyethanol; 2,6-diaminotoluene; N,N-bis(hydroxyethyl)-2,4-diaminophenetole; bis(2,4-diaminophenoxy)-1,3-propane; hydroxyethyl-2,4-diaminobenzene: 2-amino-4-(2-hydroxyethyl)amino anisole; aminoethyloxy-2,4-diaminobenzene; 2,4-diaminophenoxyacetic acid; 4,6-bis(hydroxyethyloxy) m-phenylenediamine; 2,4-diamino-5-methylphenetole; 2,4-diamino-5-hydroxyethyloxytoluene; 2,4-dimethoxy-1,3-diaminobenzene; 2,6-bis(hydroxyethylamino) toluene; and cosmetically acceptable salts thereof and combinations thereof. Preferred m-phenylenediamines include: m-phenlyenediamine; 2,4-diaminophenoxyethanol; bis(2,4-diaminophenoxy)-1,3-propane; hydroxyethyl-2,4-diaminobenzene; 2-amino-4-(2-hydroxyethyl)amino anisole; 4,6-bis(hydroxyethyloxy)m-phenylenediamine; 2,4-diamino-5-methylphenetole; 2,4-diamino-5-hydroxyethyloxytoluene; 2,4-dimethoxy-1,3- diaminobenzene; 2,6-bis(hydroxyethylamino) toluene; and cosmetically acceptable salts thereof and combinations thereof.

m-aminophenols such as: m-aminophenol; 2-hydroxy-4-carbamoylmethylamino toluene; m-carbamoylmethylamino phenol; 6-hydroxybenzomorpholine; 2-hydroxy-4-aminotoluene; 2-hydroxy-4-hydroxyethylaminotoluene (commonly known as 2-methyl-5-hydroxyethylaminophenol); 4,6-dichloro-m-aminophenol; 2-methyl-m-aminophenol; 2-chloro-6-methyl-m-aminophenol; 2-hydroxyethyloxy-5-aminophenol; 2-chloro-5-trifluoroethylaminophenol; 4-chloro-6-methyl-m-aminophenol; N-cyclopentyl-3-aminophenol; N-hydroxyethyl-4-methoxy-2-methyl-m-aminophenol; 5-amino-4-methoxy-2-methylphenol; and cosmetically acceptable salts thereof and combinations thereof. Preferred m-aminophenols include: m-aminophenol; 6-hydroxybenzomorpholine; 2-hydroxy-4-aminotoluene; 2-hydroxy-4-hydroxyethylaminotoluene (commonly known as 2-methyl-5-hydroxyethylaminophenol); 4,6-dichloro-m-aminophenol; 2-methyl-m-aminophenol; 2-chloro-6-methyl-m-aminophenol; 4-chloro-6-methyl-m-aminophenol; N-cyclopentyl-3-aminophenol; N-hydroxyethyl-4-methoxy-2-methyl-m-aminophenol; 5-amino-4-methoxy-2-methylphenol; and cosmetically acceptable salts thereof and combinations thereof.

heterocyclics such as: 1-phenyl-3-methyl-5-pyrazolone (commonly known as phenylmethylpyrazolone); 6-methoxy-8-aminoquinoline; 2,6-dihydroxy-4-methylpyridine; 5-hydroxy-1,4-benzodioxane; 3,4-methylenedioxyphenol; 4-hydroxyethylamino-1,2-methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 2,6-bis(2-hydroxyethoxy)-3,5-diaminopyridine; 4-hydroxyindole; 3-amino-5-hydroxy-2,6-dimethoxypyridine; 5,6-dihydroxyindole; 7-hydroxyindole; 5-hydroxyindole; 2-bromo-4,5-methylenedioxyphenol; 6-hydroxyindole; 3-amino-2-methylamino-6-methoxypyridine; 2-amino-3-hydroxypyridine; 2,6-diaminopyridine; 5-(3,5-diamino-2-pyridyloxy)-1,3-dihydroxypentane; 3-(3,5-diamino-2-pyridyloxy)-2-hydroxypropanol; 4-hydroxy-2,5,6-triaminopyrimidine; and cosmetically acceptable salts thereof and combinations thereof.

Particularly preferred couplers include: resorcinol; 4-chlororesorcinol; m-aminophenol; 1-naphthol; 4-amino-2-hydroxytoluene; 2-methyl-5-hydroxyethylaminophenol; 2,4-diaminophenoxyethanol; 2-methylresorcinol; bis(2,4-diaminophenoxy)-1,3-propane; 2-amino-4-hydroxyethylaminoanisole; 2-amino-3-hydroxypyridine; 1-acetoxy-2-methylnaphthalene; and cosmetically acceptable salts thereof and combinations thereof.

Combinations of any of the above described materials may also be used.

Specific examples of suitable primary intermediate and coupler combinations for use in the invention include:

resorcinol, m-aminophenol, 2-amino-4-hydroxyethyl anisole sulfate, 2,4-diaminophenoxyethanol 2HCl, 1-hydroxyethyl-4,5-diaminopyrazole sulfate and toluene-2,5-diamine sulfate;

p-phenylenediamine, m-aminophenol, N,N-bis(2-hydroxyethyl)-p-phenylenediamine sulfate and resorcinol;

p-phenylenediamine, N,N-bis(2-hydroxyethyl)-p-phenylenediamine sulfate, m-aminophenol, resorcinol, 1-naphthol and phenylmethylpyrazolone;

Other primary intermediate and coupler combinations which have been described in the literature as producing neutral black, dark black and blue black shades include: 1-(4-aminophenyl)-2-pyrrolidinemethanol and/or N-(4-aminophenyl)-4-hydroxy-2-pyrrolidinemethanol in combination with a coupler or coupler system selected from:
m-aminophenol;
resorcinol;
m-aminophenol and resorcinol;
resorcinol and 2,4-diaminophenoxyethanol;
m-aminophenol and 2-methyl-1-naphthol;
2,4-diaminophenoxyethanol and m-aminophenol, and
resorcinol and 2-methyl-1-naphthol.

Specific examples of commercially available permanent hair colorants for use in the invention include example Wella Koleston® Intense Black 22/0, TIGI® Copyright Colour Creative 1/1 or TIGI® Copyright Colour Creative 2/0. Although the precise notation systems vary slightly between different manufacturers, in all cases the shade number is the first numeral quoted (i.e. 1 or 2 for the purposes of the present invention.

The total quantity of oxidative colorant in a permanent hair colorant generally ranges from about 0.01 to about 15 wt %, by total weight primary intermediate(s) and optionally coupler(s), based on the total weight of the composition.

Darker shades are generally obtained by using higher concentrations of oxidative colorants, such as from about 3 to about 15 wt %, by total weight primary intermediate(s) and optionally coupler(s) based on the total weight of the composition.

In darker shades such as darkest brown (I.C.C. shade level 2) and black (I.C.C. shade level 1) for use in the method of the invention, primary intermediates (especially the preferred materials described above) will typically be present in the hair colorant part in an amount of about 1 to about 10 wt %, preferably about 3.5 to about 7.5%, by total weight primary intermediate(s) based on the total weight of the composition. Couplers (especially the preferred materials described above) will typically be present in the hair colorant part in an amount of about 0.1 to about 10 wt %, preferably about 1 to about 5 wt %, by total weight coupler(s) based on the total weight of the composition.

The hair colorant part may also comprise one or more compatible direct dyes, in an amount sufficient to provide colouring, particularly with regard to intensity.

Typically, such an amount will range from about 0.05 to about 4 wt %, by total weight direct dye (s) based on the total weight of the composition. Suitable direct dyes include: HC Red No. 13 (Hydrochloride); HC Yellow No. 4; HC Yellow No. 2; HC Red No. 3; 3-nitro-p-hydroxyethylaminophenol; 2-amino-6-chloro-4-nitrophenol; Acid Red 92; Disperse Black 9; HC Yellow No. 15; 4-nitro-o-phenylenediamine; Disperse Violet No. 1; HC Blue No. 2; Disperse Blue 3; Disperse Blue 377; Basic Red 51; Basic Orange 31; Basic Yellow 87; and mixtures thereof.

The hair colorant part will usually be formulated into a cosmetic preparation such as a solution, cream, lotion, gel or emulsion, and so will generally contain other components commonly associated with the formulation of such products. For example, surfactants may be used to help dissolve the primary intermediates and couplers, to assist in spreading the dye evenly over the hair, and to thicken the product so it does not drip easily while applying the product. Surfactant in the hair colorant part works as a thickener by precipitating on dilution when the hair colorant part and colour developer are mixed together. Suitable surfactants include anionic or nonionic surfactants, such as sulfates of fatty alcohols, alkanolamides of fatty alcohols, alkyl sulfonates, alkylbenzene sulfonates, oxyethylated fatty alcohols, oxyethylated nonylphenols and mixtures thereof.

If formulated as a lotion, the hair colorant part may contain organic solvents to assist in dissolving the primary intermediates and couplers. The organic solvent content of such a lotion may be up to about 20 wt %, and preferably ranges from about 1 to about 15 wt %, by weight based on the total weight of the composition.

Examples of suitable organic solvents in this context include alcohols containing up to three carbon atoms such as ethanol and isopropanol, polyhydroxy alcohols such as propylene or hexylene glycol and their lower($C_{1-4}$) alkyl ethers, such as ethoxy ethers.

Depending on the final formulated preparation, the hair colorant part may be weakly acidic, neutral or alkaline. Preferred is a pH range of about 8 to 11. Any of a wide variety of alkaline reagents can be used to adjust the pH of the hair colorant part. Such alkaline reagents include ammonium hydroxide, sodium, potassium or calcium hydroxide, sodium or potassium carbonate, sodium phosphate, sodium silicate, guanidine hydroxide, or any one of the alkylamines or alkanolamines, for example, ethylamine, triethylamine, trihydroxymethylamine, ethanolamine, diethanolamine, aminomethyl propanol, aminomethyl propanediol and the like.

Other conventionally used adjuvants which may be usefully incorporated into the hair colorant part for enhancing performance and/or consumer acceptability include:

thickeners such a fatty alcohols, starch, cellulose derivatives, paraffin oil and fatty acids;

hair-care substances such as lanolin derivatives, silicones, ceramides, proteins and protein derivatives, cholesterol, pantothenic acid, or quaternary ammonium compounds that provide hair conditioning effects, such as monomeric or polymeric quaternary ammonium compounds (for example cetyltrimonium chloride, stearyl trimonium chloride, benzalkonium chloride, behentrimonium chloride and polyquaterniums);

antioxidants to inhibit premature oxidation of oxidative colorant by air (e.g. ascorbic acid, erythorbic acid, or sodium sulfite);

fragrances or perfume oils; chelating agents; opacifying agents; buffers; dispersing agents; sequestering agents; humectants; and antimicrobials.

One or a mixture of any of the above adjuvants may be incorporated in the hair colorant part, in concentrations suitably ranging from about 0.001 to about 7.5 wt %, by weight of the individual adjuvant based on the total weight of the composition.

The colour developer for use with the hair colorant part comprises an oxidizing agent in an amount sufficient to cause formation of dye chromophores from the primary intermediates and couplers. Typically, such an amount ranges from 1% to 20%, preferably from 3% to 15%, more preferably from 6% to 12%, by weight, of the developer composition. Inorganic peroxygen materials capable of yielding hydrogen peroxide in an aqueous medium are preferred, and include: hydrogen peroxide; inorganic alkali metal peroxides (e.g. sodium periodate and sodium peroxide); organic peroxides (e.g. urea peroxide, melamine peroxide); inorganic perhydrate salt bleaching compounds (e.g. alkali metal, preferably sodium, salts of perborates, percarbonates, perphosphates, persilicates, and persulphates, which may be incorporated as monohydrates, tetrahydrates or the like); alkali metal bromates; enzymes; and mixtures thereof. Preferred is hydrogen peroxide.

The colour developer may also contain, to the extent compatible, various ingredients useful for enhancing performance and/or consumer acceptability, such as peroxide stabilizers, foam formers, etc.; and may incorporate one or more of the adjuvants referred to above.

The pH of the colour developer is typically acidic, and generally the pH is from 2.5 to 6.5, preferably from 3 to 5. The pH of the colour developer may be adjusted using a pH modifier.

According to the method of the invention, a permanent hair colorant of I.C.C shade level 1 or 2 is used to dye hair switches for the purposes of assessing the colour changes which are induced by treating the dyed hair switches with a test formulation such as a rinse-off hair treatment formulation. Typically such a rinse-off hair treatment formulation will be a surfactant-containing formulation such as a shampoo or a rinse-off conditioner.

Ina typical method according to the present invention, the dyed hair switch is soaked in the test formulation for a fixed period of time at a fixed temperature, after which the hair switch is removed & disposed of and the remaining test formulation (rinse liquor) retained for measurement.

The fixed period of time for soaking is typically in line with normal consumer wash time lengths in viva For example, during one wash of hair, hair is usually in contact with water for about 100 seconds. This would be represented by a 100 second soak. A soak of 1000 seconds would be representative of 10 washing cycles, up to a maximum of 10,000 seconds.

Similarly, the fixed temperature for soaking is typically in line with normal consumer hair washing temperatures in vivo, i.e. generally from about 20 to about 40° C. and preferably from about 30 to about 37° C. Fixing the temperature is particularly advantageous in the context of this invention since it ensures reproducibility of results.

In this way, the method of the invention enables a test formulation to be assessed for its effect on colour change under simulated in vivo conditions of washing time and/or washing temperature.

Accordingly, the method of the invention may be used to assess the potential colour protecting effect in vivo of a test formulation.

The rinse liquor is analysed for the presence of eluted colour. The analysis is preferably done by spectrophotometry. Typically, a sample of the rinse liquor is added to a cuvette and the absorbance measured with a UV-vis spectrometer at a set wavelength, according to the dye that has been used to dye the hair switch. A control cuvette (containing a sample of the original test formulation which has not been in contact with the dyed hair switch) is similarly measured. The difference in colour between the two samples may be calculated using commercially-available CIELAB software, and expressed as a delta-E value.

Advantageously, the method of the invention enables the tester to construct a colour calibration curve using serial dilutions of a test formulation (typically a surfactant solution) in which a freshly-dyed hair switch has been soaked for a prolonged period of time, such as 48 or 72 hours. In this way, calculated delta-E values may be related with dye concentration, as a proportion of the concentration of dye leached out of the hair switch under a standard set of conditions. This provides the tester with a measure of the differences in the quantity of dye leached out of the hair as a function of, for example, varying surfactant concentrations or varying soak temperatures.

The invention is further illustrated with reference to the following, non-limiting Example.

EXAMPLE 2.5 g 6" hair switches were dyed using a commercially available permanent colorant (TIGI® Copyright Colour Creative 2/0). 10 g of colorant was applied to the hair switch and rubbed through for 30 seconds using a brush until the colour was evenly distributed. The switch was then left for 35 minutes before rinsing for 2 minutes. The switch was then placed into 150 g test formulation (which may be water or surfactant solution as required) and left for a desired time, typically in line with normal consumer wash time lengths in viva For example, during one wash of hair, hair is usually in contact with water for about 100 seconds. This would be represented by a 100 second soak. A soak of 1000 seconds would be representative of 10 washes, up to a maximum of 10,000 seconds. After the set period, the switch was removed from the test formulation. A sample of the test formulation (rinse liquor) was then added to a cuvette and the absorbance measured with a UV-vis spectrometer at a set wavelength, according to the dye that is being used. For example, in the case of TIGI® Copyright Colour Creative 2/0 dye, the absorbance of a solution in water is measured at 254 nm.

The invention claimed is:

1. A method of assessing potential colour protecting effect of a hair treatment formulation, the method comprising the steps of:
   a) soaking a hair switch for a fixed period of time at a fixed temperature in the hair treatment formulation, wherein the hair switch has been artificially coloured with a permanent hair colorant having a shade level 1 or a shade level 2,
   wherein the permanent hair colorant is a two-part formulation comprising:
      a hair colorant comprising oxidative dye precursors; and
      a colour developer comprising an aqueous oxidizing agent;
      wherein mixing the hair colorant and colour developer imparts colour to the hair;
   b) removing the hair switch from the hair treatment formulation;
   c) collecting a sample of the hair treatment formulation after soaking; and
   d) analysing the sample of step c) by spectrophotometry for the presence of eluted colour, wherein the sample is measured against a control sample of the hair treatment formulation which has not been in contact with the hair switch;
   wherein:
      a colour calibration curve is constructed by carrying out the method over a series of dilutions of the hair treatment formulation;
      the shade level 1 corresponds to black and the shade level 2 corresponds to darkest brown; and
      the hair treatment formulation is a surfactant-containing rinse-off hair treatment formulation.

2. The method of claim 1, wherein the oxidative dye precursors comprise primary intermediates and couplers.

3. The method of claim 2, wherein the primary intermediates, or cosmetically acceptable salts thereof, are selected from the group consisting of p-phenylenediamine, p-toluenediamine, p-aminophenol, 3-methyl-p-aminophenol, N,N-bis(2-hydroxyethyl)-p-phenylenediamine, 2-hydroxyethyl-p-phenylenediamine, 1-hydroxyethyl-4,5-diaminopyrazole, and combinations thereof.

4. The method of claim 2, wherein the couplers, or cosmetically acceptable salts thereof, are selected from the group consisting of resorcinol, 4-chlororesorcinol, m-aminophenol, 1-naphthol, 4-amino-2-hydroxytoluene, 2-methyl-5-hydroxyethylaminophenol, 2,4-diaminophenoxyethanol, 2-methylresorcinol, bis(2,4-diaminophenoxy)-1,3-propane, 2-amino-4-hydroxyethylaminoanisole, 2-amino-3-hydroxypyridine, 1-acetoxy-2-methylnaphthalene, and combinations thereof.

5. The method of claim 2, wherein the primary intermediate and coupler are present in the oxidative dye precursor at a molar ratio from 0.95 to 1.05.

6. The method of claim 2, wherein the primary intermediate is present in an amount of about 1 wt % to about 10 wt % based on the total weight of the hair colorant.

7. The method of claim 2, wherein the coupler is present in an amount of about 0.1 wt % to about 10 wt % based on the total weight of the hair colorant.

8. The method of claim 1, wherein the oxidative dye precursors comprise of a combination of primary intermediates selected from the group consisting of 1-(4-aminophenyl)-2-pyrrolidinemethanol, N-(4-aminophenyl)-4-hydroxy-2-pyrrolidinemethanol, and combinations thereof and couplers or a coupler system selected from the group consisting of m-aminophenol, resorcinol, m-aminophenol and resorcinol, resorcinol and 2,4-diaminophenoxyethanol, m-aminophenol and 2-methyl-lnaphtol, 2,4-diaminophenoxyethanol and m-aminophenol, and resorcinol and 2-methyl-1-naphthol.

9. The method of claim 1, wherein the surfactant-containing rinse-off hair treatment formulation is a shampoo or a rinse-off conditioner.

10. The method of claim 1, wherein the fixed period of time is from 100 seconds to 10,000 seconds.

11. The method of claim 10, wherein the fixed period of time is from 100 seconds to 1000 seconds.

12. The method of claim 1, wherein the fixed temperature is from about 20° C. to about 40° C.

13. The method of claim 12, wherein the fixed temperature is from about 30° C. to about 37° C.

14. A method of assessing potential colour protecting effect of a hair treatment formulation, the method comprising the steps of:
   a) soaking a hair switch for a fixed time at a fixed temperature in the hair treatment formulation, wherein the hair switch has been artificially coloured with a permanent hair colorant comprising:
      a primary intermediate, or a cosmetically acceptable salt thereof, selected from the group consisting of 1-(4-aminophenyl)-2-pyrrolidinemethanol, N-(4-aminophenyl)-4-hydroxy-2-pyrrolidinemethanol, and combinations thereof;
      one or more couplers, or a cosmetically acceptable salt thereof; and
      a colour developer comprising an aqueous oxidizing agent;
   b) removing the hair switch from the hair treatment formulation; and
   c) collecting a sample of the hair treatment formulation after soaking; and
   d) analysing the sample by spectrophotometry for the presence of eluted colour, wherein the sample is measured against a control sample of the hair treatment formulation which has not been in contact with the hair switch;
   wherein:
      a colour calibration curve is constructed by carrying out the method over a series of dilutions of the test formulation; and
      the hair treatment formulation is a surfactant-containing rinse-off hair treatment formulation.

15. The method of claim 14, wherein the fixed time period is from 100 seconds to 10,000 seconds.

16. The method of claim 14, wherein the fixed temperature is from about 30° C. to about 37° C.

17. The method of claim 14, wherein the one or more couplers, or a cosmetically acceptable salt thereof, are selected from the group consisting of resorcinol, 4-chlororesorcinol, m-aminophenol, 1-naphthol, 4-amino-2-hydroxytoluene, 2-methyl-5-hydroxyethylaminophenol, 2,4-diaminophenoxyethanol, 2-methylresorcinol, bis(2,4-diaminophenoxy)-1,3-propane, 2-amino-4-hydroxyethylaminoanisole, 2-amino-3-hydroxypyridine, 1-acetoxy-2-methylnaphthalene, 2-methyl-1-naphthol, and combinations of two or more thereof.

* * * * *